(12) United States Patent
Masuda et al.

(10) Patent No.: US 7,709,015 B2
(45) Date of Patent: *May 4, 2010

(54) PERSONAL CARE COMPOSITION COMPRISING HYDROPHOBIC GEL

(75) Inventors: Hisatoshi Masuda, Moriyama (JP); Mayu Ishigami, Ashiya (JP); George Endel Deckner, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 11/897,082

(22) Filed: Aug. 29, 2007

(65) Prior Publication Data

US 2008/0057014 A1    Mar. 6, 2008

Related U.S. Application Data

(63) Continuation of application No. 10/740,254, filed on Dec. 18, 2003, now Pat. No. 7,270,828, which is a continuation of application No. PCT/US01/19702, filed on Jun. 20, 2001.

(51) Int. Cl.
*A61K 8/02* (2006.01)
*A61Q 1/04* (2006.01)
*A61Q 1/06* (2006.01)

(52) U.S. Cl. .................................. 424/401; 424/64
(58) Field of Classification Search ................ 424/401, 424/64
See application file for complete search history.

(56) References Cited

U.S. PATENT DOCUMENTS

| 5,165,917 A | * | 11/1992 | Zabotto et al. ............ 424/70.12 |
| 5,587,149 A | | 12/1996 | Punto et al. |
| 5,681,551 A | * | 10/1997 | Nojima ........................ 424/64 |
| 6,241,976 B1 | | 6/2001 | Esser et al. |
| 6,248,336 B1 | | 6/2001 | McDermott |
| 6,361,783 B2 | | 3/2002 | Moaddel et al. |
| 2004/0219122 A1 | | 11/2004 | Masuda et al. |

FOREIGN PATENT DOCUMENTS

| WO | WO 96/24325 | | 8/1996 |
| WO | WO 96-36308 | | 11/1996 |
| WO | WO 9717939 A1 | * | 5/1997 |
| WO | WO 9947111 | | 9/1999 |
| WO | WO9956716 A1 | | 11/1999 |
| WO | WO 00/61094 | | 10/2000 |
| WO | WO 01/12137 | | 2/2001 |
| WO | WO 01/12138 | | 2/2001 |
| WO | WO 01/12139 | | 2/2001 |
| WO | WO 01/12152 | | 2/2001 |
| WO | WO 03/000223 A1 | | 1/2003 |

* cited by examiner

*Primary Examiner*—Yong S Chong
*Assistant Examiner*—Jody L Karol
(74) *Attorney, Agent, or Firm*—S. Robert Chuey; Megan C. Hymore

(57) ABSTRACT

Disclosed is a polyol-in-silicone emulsion consisting essentially of:
(i) an alkyl dimethicone copolyol having an HLB of from about 4 to about 6, and a molecular weight of from about 10,000 to about 20,000, wherein the alkyl group is made of about 10 to about 22 carbons; and
(ii) a polyol, wherein the weight ratio of the alkyl dimethicone copolyol to the polyol is from about 100:1 to about 2:8;
methods to make such a polyol-in-silicone emulsion, as well as an anhydrous personal care composition comprising by weight:
(a) from about 0.01% to about 15% of an alkyl dimethicone copolyol having an HLB of about 4-6, and a molecular weight of from about 10,000 to about 20,000, wherein the alkyl group is made of about 10 to about 22 carbons;
(b) from about 0.01% to about 35% of a polyol, wherein the weight ratio of the alkyl dimethicone copolyol to the polyol is from about 100:1 to about 2:8; and
wherein the composition is substantially free of water.

5 Claims, No Drawings

PERSONAL CARE COMPOSITION COMPRISING HYDROPHOBIC GEL

CROSS REFERENCE TO RELATED APPLICATIONS

This application is a continuation of application Ser. No. 10/740,254 filed Dec. 18, 2003 now U.S. Pat. No. 7,270,828, which is a continuation of prior copending International Application No. PCT/US01/19702, filed Jun. 20, 2001, designating the U.S.

FIELD OF THE INVENTION

The present invention relates to a polyol-in-silicone emulsion, personal care compositions comprising the polyol-in-silicone emulsion, and methods of making the polyol-in-silicone emulsion. The present invention also relates to anhydrous personal care compositions comprising an alkyl dimethicone copolyol compound and a polyol. The composition is useful for making various personal care compositions, and particularly lipophilic compositions such as lipsticks and foundations.

BACKGROUND

Lipsticks are primarily made of lipophilic or hydrophobic materials. Lipsticks designed for providing a moisturizing benefit to the lips further contain water, polar solvents, or other moisturizing components which are more or less hydrophilic. The use of association structures have been suggested to bind such moisturizing components in the lipophilic matrix of the lipstick. While such lipstick compositions provide a favorable moisturizing benefit to the lips, they were not completely satisfactory in terms of physical stability, color stability, and sweat resistance.

Physical stability relates to the stability of the stick during storage and upon use. For example, a stable stick does not deform during storage at ambient temperature, and does not bend or break upon normal condition use. Color stability relates to the stability of color during storage and after application on the lip. It has been known that lipsticks containing a high amount of moisturizing components have the tendency to change color over time after application on the lip. Sweating is a phenomena seen on the surface of sticks, and is believed to be due to oils and/or solvents separating and leaking out of the lipophilic matrix of the stick. Sweating provides a negative appearance to the user.

Stability is also an important requirement for other lipophilic or anhydrous compositions such as liquid and powder foundations. For foundations, stability relates to color, viscosity, and phase condition.

Anhydrous cosmetic foundations containing alkyl dimethicone copolyols and polyols are disclosed, for example, in PCT publications WO 01/12137, WO 01/12138, WO 01/12139, and WO 01/12152. While such compositions are believed to provide physical stability, further improvement is desired, particularly for applying to lipophilic lipstick compositions.

Based on the foregoing, there is a need for a personal care composition which has improved stability over a wide range of product forms, and which can be made using conventional equipment for making personal care compositions. There is also a need for an anhydrous composition which as improved physical stability, improved color stability, and improved sweat resistance, while also providing moisturizing benefit to the lips.

SUMMARY

The present invention is directed to a polyol-in-silicone emulsion consisting essentially of:
(i) an alkyl dimethicone copolyol having an HLB of from about 4 to about 6, and a molecular weight of from about 10,000 to about 20,000, wherein the alkyl group is made of about 10 to about 22 carbons; and
(ii) a polyol, wherein the weight ration of the alkyl dimethicone copolyol to the polyol is from about 100:1 to about 2:8.

The present invention is also directed to methods to make such a polyol-in-silicone emulsion.

The present invention is also directed to an anhydrous personal care composition comprising by weight:
(a) from about 0.01% to about 15% of an alkyl dimethicone copolyol having an HLB of about 4-6, and a molecular weight of from about 10,000 to about 20,000, wherein the alkyl group is made of about 10 to about 22 carbons;
(b) from about 0.01% to about 35% of a polyol, wherein the weight ratio of the alkyl dimethicone copolyol to the polyol is from about 100:1 to about 2:8; and wherein the composition is substantially free of water.

These and other features, aspects, and advantages of the present invention will become evident to those skilled in the art from a reading of the present disclosure with the appended claims.

DETAILED DESCRIPTION

The following is a list of definitions for terms used herein.

"Comprising" means that other steps and other ingredients which do not affect the end result can be added. This term encompasses the terms "consisting of" and "consisting essentially of".

All percentages are by weight of total composition unless specifically stated otherwise.

All cited references are incorporated herein by reference in their entireties. Citation of any reference is not an admission regarding any determination as to its availability as prior art to the claimed invention.

All ratios are weight ratios unless specifically stated otherwise.

The present invention, in its product and process aspects, is described in detail as follows.

Alkyl Dimethicone Copolyol

In one embodiment, the present invention relates to a polyol-in-silicone emulsion consisting essentially of an alkyl dimethicone copolyol, a polyol, and optional hydrophilic skin treatment agent. In another embodiment, the present invention relates to an anhydrous personal care composition comprising an alkyl dimethicone copolyol, the alkyl dimethicone copolyol preferably being incorporated in the form of a polyol-in-silicone emulsion. In such anhydrous personal care composition, the alkyl dimethicone copolyol is preferably comprised by weight of the entire composition at from about 0.01% to about 15%, preferably from about 0.3% to about 5%, wherein the weight ratio of the alkyl dimethicone copolyol to the polyol is from about 100:1 to about 2:8.

The alkyl dimethicone copolyol of the present invention is a nonionic polysiloxane copolymer having emulsifying ability, comprising a methylpolysiloxane moiety, an alkyl methylpolysiloxane moiety, and a poly(oxyalkylene)methylpolysiloxane moiety; having an HLB from about 4 to about 6, and a molecular weight of from about 10,000 to about 20,000, wherein the alkyl group is made of from about 10 to about 22 carbons. The HLB value is a theoretical index value which describes the hydrophilicity-hydrophobicity balance of a specific compound. Generally, it is recognized that the HLB index ranges from 0 (very hydrophobic) to 40 (very hydrophilic). The HLB value of the lipophilic surfactants may be found in tables and charts known in the art, or may be calculated with the following general equation: HLB=7+(hydrophobic group values)+(hydrophilic group values). The HLB and methods for calculating the HLB of a compound are explained in detail in "Surfactant Science Series, Vol. 1: Nonionic Surfactants", pp 606-13, M. J. Schick (Marcel Dekker Inc., New York, 1966).

Suitable alkyl dimethicone copolyols herein are those which have the following formulation (I):

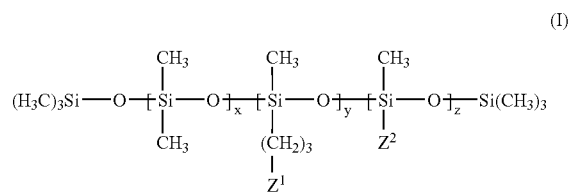

wherein $Z^1$ is $O(C_2H_4O)_p(C_3H_6O)_qH$, p is from 0 to about 50, q is from 0 to about 30, where p and q are not 0 at the same time; x is from 1 to about 200, y is from 1 to about 40, and z is from 1 to about 100, and $Z^2$ is an alkyl group having from about 10 to about 22 carbons, preferably from about 16 to about 18 carbons.

Highly preferred alkyl dimethicone copolyols include cetyl dimethicone copolyol and stearyl dimethicone copolyol. A highly preferred commercially available alkyl dimethicone copolyol includes cetyl dimethicone copolyol, also called Methylpolysiloxane Cetylmethylpolysiloxane Poly(oxyethylene oxypropylene) Methylpolysiloxane Copolymer, having an HLB of about 5 and a molecular weight of about 13,000 having a tradename ABIL EM90 available from Goldschmidt Personal Care.

Polyol

In one embodiment, the polyol of the present invention provides a polyol-in-silicone emulsion together with the alkyl dimethicone copolyol and optional hydrophilic skin treatment agent. In another embodiment, the present invention relates to an anhydrous personal care composition comprising the polyol, the polyol preferably being incorporated in the form of a polyol-in-silicone emulsion. In such anhydrous personal care composition, the polyol is preferably comprised by weight of the entire composition at from about from about 0.01% to about 35%, preferably from about 0.1% to about 10%, wherein the weight ratio of the alkyl dimethicone copolyol to the polyol is from about 100:1 to about 2:8.

Polyols useful herein include polyhydric alcohols such as glycerin, 1,3-butylene glycol, propylene glycol, hexylene glycol, propane diol, ethylene glycol, diethylene glycol, dipropylene glycol, diglycerin, sorbitol, and other sugars which are in liquid form at ambient temperature. Also useful herein are water soluble alkoxylated nonionic polymers such as polyethylene glycol.

Commercially available polyols herein include: glycerin available from Asahi Denka; propylene glycol with tradename LEXOL PG-865/855 available from Inolex, 1,2-PROPYLENE GLYCOL USP available from BASF; 1,3-butylene glycol available from Daisel Kagaku Kogyo; dipropylene glycol with the same tradename available from BASF; and diglycerin with tradename DIGLYCEROL available from Solvay GmbH.

Polyol-In Silicone Emulsion

The present invention relates to a polyol-in-silicone emulsion consisting essentially of the alkyl dimethicone copolyol, the polyol, and optional hydrophilic skin treatment agent, wherein the weight ratio of the alkyl dimethicone copolyol to the polyol is from about 100:1 to about 2:8, preferably from about 9:1 to about 2:8; and the optional hydrophilic skin treatment agent is included in an amount soluble in the polyol. In a highly preferable anhydrous lipstick embodiment, the weight ratio of the alkyl dimethicone copolyol to the polyol is about 3:7.

Alkyl dimethicone copolyols are known as emulsifiers for formulation of cosmetic water-in-oil creams and lotions, such as disclosed in the brochure of "ABIL EM90" published by Goldschmidt Personal Care on March 1999. It has been surprisingly found that the alkyl dimethicone copolyol of the present invention forms a stable polyol-in-silicone emulsion by mixing with polyols, such polyol-in-silicone emulsions useful for making various personal care compositions, and particularly useful for making compositions of lipophilic or anhydrous nature. Of importance is that, in order to obtain a stable polyol-in-silicone emulsion, the polyol-in-silicone emulsion consists essentially of the alkyl dimethicone copolyol, the polyol, and optional hydrophilic skin treatment agent i.e, the polyol-in-silicone emulsion preferably does not contain components other than the alkyl dimethicone copolyol, the polyol, and the hydrophilic skin treatment agent. Materials which may interfere with the stability of the polyol-in-silicone emulsion, and thus the polyol-in-silicone emulsion should be free of, are: other emulsifiers; lower alcohols; oils including esters and hydrocarbon oils; thickeners including fatty acid, fatty alcohol, and waxes; and more than 0.01% water by weight of the polyol-in-silicone emulsifier.

The polyol-in-silicone emulsion can hold the polyol in a stable manner. Polyols are materials highly preferred for use in personal care compositions, as it provides moisturizing benefit to the skin, and can also be a solvent for other hydrophilic materials, such as the hydrophilic skin treatment agents discussed below. By changing the level and type of carrier, various personal care compositions containing the polyol-in-silicone emulsion can be made, such as: color cosmetics for the lips, face (foundation), cheeks (blushers), and eyelids (eyeshadow), in the form of stick, gel, cream, or powder; make-up removers; skin care creams; and antiperspirant sticks and creams. Personal care compositions containing the polyol-in-silicone emulsion provide improved physical stability, such as in phase condition and viscosity. Without being bound by theory, it is believed that the polyol-in-silicone emulsion herein possesses excellent thermal stability, thereby being stable under environments beyond ambient temperature. Personal care compositions of the present invention preferably comprise by weight of from about 0.1% to about 20%, more preferably from about 1% to about 10% of the polyol-in-silicone emulsion.

The polyol-in-silicone emulsion of the present invention is particularly useful for incorporating polyols into lipophilic or anhydrous compositions such as lipsticks, and liquid and powder foundations. By "anhydrous", what is meant is that water is not actively included in the composition. However, the anhydrous compositions of the present invention do not exclude the use of components which may carry an insignificant amount of water as a byproduct or impurity. For example, it is known in the art that the polyols mentioned above may carry a small percentage of water. Such small amount of water is acceptable in the present composition. Typically, water should be included at a level of less than about 1.0%, preferably less than about 0.2% of the entire anhydrous composition.

The polyol-in-silicone emulsion herein is preferably made by a method comprising mixing the alkyl dimethicone copolyol with the polyol at a speed of at least about 1000 rpm, preferably from about 1000 rpm to about 3000 rpm, more preferably from about 1500 rpm to about 2000 rpm and at a temperature of at least about 30° C., preferably from about 30° C. to about 80° C., more preferably from about 40° C. to about 70° C.

The polyol may be pre-heated before mixing with the alkyl dimethicone copolyol. When hydrophilic skin treatment agents are included in the composition, they are pre-dissolved in the polyol prior to mixing with the alkyl dimethicone. Heating may be added at this pre-dissolving step. In one preferred embodiment, the polyol is heated to a temperature of at least about 75° C. in order to dissolve hydrophilic skin treatment agents such as niacinamide, preferably from about 75° C. to about 90° C., more preferably from about 80° C. to about 85° C.; and mixing at low speed, as needed; prior to mixing with the alkyl dimethicone copolyol.

Except for the hydrophilic skin treatment agents, other carrier components are not added during the process of making the polyol-in-silicone emulsion.

The mixing at any step of making the polyol-in-silicone emulsion can be provided by any high shear mixer known in the art, such as those known as Disper. The mixing required for providing the polyol-in-silicone emulsion of the present invention is relatively mild, and thus the polyol-in-silicone emulsion can be made using conventional equipment for making personal care compositions.

The polyol-in-silicone emulsion thus obtained is then mixed with the carrier using conventional mixing means.

Hydrophilic Skin Treatment Agent

The polyol-in-silicone emulsion and the personal care composition of the present invention may comprise a skin treatment agent of hydrophilic nature in an amount soluble in the polyol above, preferably from about 0.001% to about 20%, more preferably from about 0.01% to about 10% by weight of the personal care composition. When comprised in personal care compositions, the hydrophilic skin treatment agents herein are incorporated by first solubilizing in the polyol, and preferably, formed into the polyol-in-silicone emulsion. Hydrophilic skin treatment agents may be included in various personal care compositions.

It has been surprisingly found that the hydrophilic skin treatment agent, together with the alkyl dimethicone copolyol and the polyol, forms a stable polyol-in-silicone emulsion, when mixed in an amount soluble in the polyol. Thus, lipophilic and/or anhydrous compositions may contain hydrophilic skin treatment agents in a stable manner by incorporating them via the polyol-in-silicone emulsion of the present invention.

Hydrophilic skin treatment agents useful herein include niacinamide, panthenol, bacterial cultured mediums, allantoin, sodium lactate, PCA soda, amino acids, urea, sodium hyaluronate, chondroitin sulfate, collagen, elastin, pectin, carageenan, sodium alginate, trehalose, tuberose saccharide, chitin derivatives, chitosan derivatives, and mixtures thereof. Niacinamide and panthenol are commercially available, for example, by Roche. Sodium hyaluronate is available in tradenames ACTIMOIST available from Active Organics, AVLAN SODIUM HYALURONATE series available from Intergen, HYALURONIC ACID Na available from Ichimaru Pharcos Carrier The present invention relates to personal care compositions comprising a carrier in addition to the alkyl dimethicone copolyol and the polyol mentioned above. When the personal care composition is anhydrous, the alkyl dimethicone copolyol and the polyol may be made in any method suitable for the artisan. For providing a stable composition, however, the alkyl dimethicone copolyol and the polyol are incorporated in the composition in the form of a polyol-in-silicone emulsion. The personal care composition of the present invention preferably comprises from about 0.01% to about 65% of the polyol-in-silicone emulsion.

When the alkyl dimethicone copolyol and the polyol are incorporated in the composition in the form of a polyol-in-silicone emulsion, the polyol-in-silicone emulsion is prepared first, and then mixed with the carrier to provide the composition. When a hydrophilic skin treatment agent is included in the composition, the hydrophilic skin treatment agent may be exceptionally added to the polyol-in-silicone emulsion. The carrier is selected to provide the desired use and characteristic for the personal care composition. Materials which may interfere with the stability of the polyol-in-silicone emulsion, such as: other emulsifiers; lower alcohols; oils including esters and hydrocarbon oils; thickeners including fatty acid, fatty alcohol, and waxes; and more than 0.01% water by weight of the polyol-in-silicone emulsifier; may be incorporated in the carrier, but are not added during the process of making the polyol-in-silicone emulsion. Such materials can be stably incorporated in the personal care compositions, by mixing with the polyol-in-silicone emulsion after the polyol-in-silicone is made according to the method described above.

For providing color cosmetics, for the lips, face (foundation), cheeks (blushers), and eyelids (eyeshadow), in the form of stick, gel, cream, or powder; the carrier comprises an oil and a pigment. To form a stick or viscous cream/gel, the color cosmetic composition may further comprise a thickening agent. To form a powder, the color cosmetic composition may further comprise an oil for use as a binding material. For stable incorporation of the oils and pigments, the color cosmetic composition may further comprise additional emulsifiers. For wear resistance, the color cosmetic composition may further comprise a film forming agent. The compositions of the present invention are particularly useful for providing color cosmetics of lipophilic or anhydrous nature.

For providing antiperspirant sticks and creams, the carrier comprises a thickening agent and an antiperspirant active.

For providing skin care creams, the carrier comprises an oil, typically a thickening agent, and optionally other agents for providing benefit to the skin, such as hydrophilic skin treatment agents, and whitening agents.

For providing make-up removers, the carrier comprises a detersive surfactant and water, and optionally an oil.

Thickening Agents

The carrier may contain a thickening agent for providing a viscous liquid or solid composition, such as solid waxes, gelling agents, inorganic thickeners, oil soluble polymers, fatty compounds, and mixtures thereof.

For providing lipstick or stick foundation compositions, a solid wax is preferably used. The solid wax is comprised in such compositions by weight of the entire composition at from about 10% to about 20%, preferably 12% to about 15%. The amount of the solid wax is controlled to provide the desired hardness and strength to the product. The solid waxes useful herein are paraffin wax, microcrystalline wax, ozokerite was, ceresin wax, carnauba wax, candelilla wax, eicosanyl behenate, and mixtures thereof. A mixture of waxes is preferably used. Commercially available solid waxes useful herein include: Candelilla wax NC-1630 available from Noda wax, Ozokerite wax SP-1021 available from Strahl & Pitsh, and Eicosanyl behenate available from Cas Chemical.

Gelling agents may be included in the carrier as a thickening agent. Gelling agents include esters and amides of fatty acid gellants, hydroxy acids, hydroxy fatty acids, cholesterolic materials, lanolinolic materials, other amide gellants, and crystalline gellants. N-acyl amino acid amides useful herein are prepared from glutamic acid, lysine, glutamine, aspartic acid and mixtures thereof. Particularly preferred are n-acyl glutamic acid amides corresponding to the following formula:

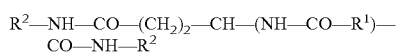

$R^2—NH—CO—(CH_2)_2—CH—(NH—CO—R^1)—CO—NH—R^2$ wherein $R^1$ is an aliphatic hydrocarbon radical having from about 12 to about 22 carbon atoms, and $R^2$ is an aliphatic hydrocarbon radical having from about 4 to about 12 carbon atoms. Non-limiting examples of these include n-lauroyl-L-glutamic acid dibutyl amide, n-stearoyl-L-glutamic acid diheptyl amide, and mixtures thereof. Most preferred is n-lauroyl-L-glutamic acid dibutyl amide, also referred to as dibutyl lauroyl glutamide. This material is commercial available with tradename Gelling agent GP-1 available from Ajinomoto. Amidoamines of the following general formula are useful herein:

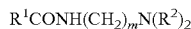

$R^1CONH(CH_2)_mN(R^2)_2$ wherein $R^1$ is a residue of $C_{11}$ to $C_{24}$ fatty acids, $R^2$ is a $C_1$ to $C_4$ alkyl, and m is an integer from 1 to 4. Preferred amidoamine useful in the present invention includes stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, and mixtures thereof; more preferably stearamidopropyldimethylamine, stearamidoethyldiethylamine, and mixtures thereof. Other gelling agents suitable for use in the compositions include 12-hydroxystearic acid, esters of 12-hydroxystearic acid, amides of 12-hydroxystearic acid and combinations thereof. These preferred gellants include those which correspond to the following formula:

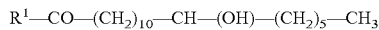

$R^1—CO—(CH_2)_{10}—CH—(OH)—(CH_2)_5—CH_3$ wherein $R^1$ is $R^2$ or $NR^2R^3$; and $R^2$ and $R^3$ are hydrogen, or an alkyl, aryl, or arylalkyl radical which is branched linear or cyclic and has from about 1 to about 22 carbon atoms; preferably, from about 1 to about 18 carbon atoms. $R^2$ and $R^3$ may be either the same or different; however, at least one is preferably a hydrogen atom. Preferred among these gellants are those selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, triester of glycerin and hydroxystearic acid known as trihydroxystearin, and mixtures thereof; even more preferably, 12-hydroxystearic acid, isopropyl amide of 12-hydroxystearic acid, and combinations thereof.

Commercially available hydroxystearin compounds useful herein include 12-hydroxystearic acid (cosmetic grade) available from Kawaken and CasChem, and trihydroxystearin with tradenames Thixcin R available from Rheox, Flowtone R available from ECC America, and Rheocin available from United Catalysts.

Suitable amide gellants include disubstituted or branched monoamide gellants, monosubstituted or branched diamide gellants, triamide gellants, and combinations thereof, excluding the n-acyl amino acid derivatives selected from the group consisting of n-acyl amino acid amides, n-acyl amino acid esters prepared from glutamic acid, lysine, glutamine, aspartic acid, and combinations thereof, and which are specifically disclosed in U.S. Pat. No. 5,429,816.

Alkyl amides or di- and tri-basic carboxylic acids or anhydrides suitable for use in the composition include alkyl amides of citric acid, tricarballylic acid, aconitic acid, nitrilotriacetic acid, succinic acid and itaconic acid such as 1,2,3-propane tributylamide, 2-hydroxy-1,2,3-propane tributylamide, 1-propene-1,2,3-triotylamide, N,N',N''-tri(acetodecylamide)amine, 2-dodecyl-N,N'-dihexylsuccinamide, and 2 dodecyl-N,N'-dibutylsuccinamide. Preferred are alkyl amides of di-carboxylic acids such as di-amides of alkyl succinic acids, alkenyl succinic acids, alkyl succinic anhydrides and alkenyl succinic anhydrides, more preferably 2-dodecyl-N,N'-dibutylsuccinamide.

Other gellants useful herein include anthryl derivatives such as 2,3-bis n-decyloxyanthracene, hybrids of steroids and anthryl derivatives such as cholesterol anthraquinone-2-carboxylate, alpha amino acid oligomers such as N-benzyl oxycarbonyl-1-valyl-L-valine-n-octadecyl amide, organometallics such as mononuclear copper beta-diketonates and binuclear Cu and Rh tetracarboxylates, dextrin derivatives such as dextrin palmitate and dextrin myristate, and decaglycerin pentastearic acid.

Inorganic thickeners useful as thickening agents herein include oil swelling clays, oil soluble clays, silica, and mixtures thereof. The oil swelling clay material useful herein are those which function as a thickener for the composition. Thus, the amount of oil swelling clay material included is adjusted depending on the desired viscosity and hardness of the composition. For providing lipstick compositions, the oil swelling clay material is comprised by weight of the entire composition at from about 0.1% to about 1%, preferably from about 0.2% to about 0.5%. Oil swelling clay materials useful herein include hectorite, bentonite, montmorillonite, and bentone clays which have been modified to be compatible with oil. Preferably, the modification is quaternization with an ammonium compound. Preferable oil swelling clay materials include quaternary ammonium modified hectorite. Commercially available oil swelling clay materials include benzyldimethyl stearyl ammonium hectorite with tradename Bentone 38 CG OR available from Rheox. Inc. The silica thickening agents commercially available are the Aerosil series (200, 300, 200CF, and 300CF) available from Degussa.

Oil soluble polymers are useful as thickeners. Oil soluble polymers useful herein include guar gum which is a resinous material derived from the ground endosperm of cyanopsis tetragonoloba and close relatives.

Fatty compounds are useful as thickening agents. The fatty compound useful herein have a melting point of 25° C. or higher, and is selected from the group consisting of fatty alcohols, fatty acids, fatty alcohol derivatives, fatty acid derivatives, and mixtures thereof. It is understood that the fatty compound thickeners herein may also provide emollient benefits.

The fatty alcohols useful herein are those having from about 14 to about 30 carbon atoms, preferably from about 16 to about 22 carbon atoms. These fatty alcohols are saturated and can be straight or branched chain alcohols. Nonlimiting examples of fatty alcohols include, cetyl alcohol, stearyl alcohol, behenyl alcohol, and mixtures thereof.

The fatty acids useful herein are those having from about 10 to about 30 carbon atoms, preferably from about 12 to about 22 carbon atoms, and more preferably from about 16 to about 22 carbon atoms. These fatty acids are saturated and can be straight or branched chain acids. Also included are diacids, triacids, and other multiple acids which meet the requirements herein. Also included herein are salts of these fatty acids. Nonlimiting examples of fatty acids include lauric acid, palmitic acid, stearic acid, behenic acid, sebacic acid, and mixtures thereof. Fatty acid soaps are also useful herein. Nonlimiting examples of fatty acid soaps include natural soaps with Li, Na, Ca, Ba, and Al metals, including aluminium oleate and aluminium laurate.

The fatty alcohol derivatives and fatty acid derivatives useful herein include alkyl ethers of fatty alcohols, alkoxylated fatty alcohols, alkyl ethers of alkoxylated fatty alcohols, esters of fatty alcohols, fatty acid esters of compounds having esterifiable hydroxy groups, hydroxy-substituted fatty acids, and mixtures thereof. Nonlimiting examples of fatty alcohol derivatives and fatty acid derivatives include materials such as methyl stearyl ether; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; $C_1$-$C_{30}$ alkyl ethers of the ceteth, steareth, and ceteareth compounds just described; polyoxyethylene ethers of behenyl alcohol; ethyl stearate, cetyl stearate, cetyl palmitate, stearyl stearate, myristyl myristate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, glyceryl monostearate, glyceryl distearate, glyceryl tristearate, and mixtures thereof.

Commercially available materials useful herein include: myristyl myristate available from Croda with tradename Crodamol MM; cetyl alcohol, stearyl alcohol, and behenyl alcohol having tradenames KONOL series available from Shin Nihon Rika (Osaka, Japan), and NAA series available from NOF (Tokyo, Japan); pure behenyl alcohol having tradename 1-DOCOSANOL available from WAKO (Osaka, Japan), various fatty acids having tradenames NEO-FAT available from Akzo (Chicago Ill., USA), HYSTRENE available from Witco Corp. (Dublin Ohio, USA), and DERMA available from Vevy (Genova, Italy).

Fatty compounds useful herein include fatty acid sugar esters having $C_{1-30}$ monoester or polyester of sugars and one or more carboxylic acid moieties, preferably a sucrose polyester in which the degree of esterification is 7-8, and in which the fatty acid moieties are $C_{18}$ mono- and/or di-unsaturated and behenic, in a molar ratio of unsaturates:behenic of 1:7 to 3:5, more preferably the octaester of sucrose in which there are about 7 behenic fatty acid moieties and about 1 oleic acid moiety in the molecule, e.g., sucrose ester of cottonseed oil fatty acids. The thickening capability of these compounds are further enhanced by adding about 1-3% of lower alcohols such as ethanol in the composition. Preferred compounds in this group include sucrose esterified with fatty acids derived from hardened, high-erucic acid rapeseed oil coded as SEFA behenate available from the Procter & Gamble Company. Fatty compounds useful herein include aluminium salt of phophatididic acid, steroid derivatives, cholesterol esters, and Na, Li, K, and NH4 salts of 12-hydroxyoctadecanoic acid.

Pigments

For providing color cosmetic compositions, the carrier may contain pigments. For providing foundations and other color cosmetic compositions, the pigments are preferably comprised by weight of the entire composition at from about 5.0% to about 95%, more preferably 10% to about 90%. For providing lipstick compositions, the pigments are preferably comprised by weight of the entire composition at from about 1% to about 30%, preferably from about 2% to about 20%, more preferably from about 10% to about 15%. The amount and type of pigments are selected depending on the desired characteristic of the product, for example, shade, coverage, UV protection benefit, and various skin feel.

The materials useful herein are clay mineral powders such as talc, mica, sericite, silica, magnesium silicate, synthetic fluorphlogopite, calcium silicate, aluminum silicate, bentonite and montomorillonite; pearl pigments such as alumina, barium sulfate, calcium secondary phosphate, calcium carbonate, titanium oxide, finely divided titanium oxide, zirconium oxide, zinc oxide, hydroxy apatite, iron oxide, iron titate, ultramarine blue, Prussian blue, chromium oxide, chromium hydroxide, cobalt oxide, cobalt titanate, titanium oxide coated mica; organic powders such as polyester, polyethylene, polystyrene, methyl metharylate resin, cellulose, 12-nylon, 6-nylon, styrene-acrylic acid copolymers, poly proprylene, vinyl chloride polymer, tetrafluoroethylene polymer, boron nitride, fish scale guanine, laked tar color dyes, and laked natural color dyes.

A certain percentage of spherical pigments can be used. In a preferred embodiment, the materials are selected depending on the oil absorbing capability of the pigments.

Hydrophobically treated pigments can also be used. Such hydrophobically treated pigments are made by treating the base material, as above, with a hydrophobical treatment agent, including: silicone such as Methicone, Dimethicone and perfluoroalkylsilane; fatty material such as stearic acid; metal soap such as aluminium dimyristate; aluminium hydrogenated tallow glutamate, hydrogenated lecithin, lauroyl lysine, aluminium salt of perfluoroalkyl phosphate, and mixtures thereof.

Oils

Oils are typically comprised in the carrier for providing various personal care compositions. The oils herein may act as a solvent or continuous phase for the remaining components of the carrier, and/or provide emollient effects, binding effects, and softening effects. Lipophilic and/or anhydrous personal care compositions may contain from about 30% to about 80% oil, preferably from about 50% to about 70% oil.

The oils can be volatile or nonvolatile. For providing liquid foundations, volatile oils are generally comprised for preventing a sticky feel, and providing good spreadability.

The volatile silicone oils useful herein are selected from those having a boiling point of from about 60 to about 260° C., preferably those having from 2 to 7 silicon atoms.

The volatile silicone oils useful herein include polyalkyl or polyaryl siloxanes with the following structure (I):

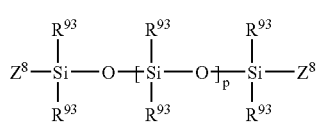

wherein $R^{93}$ is independently alkyl or aryl, and p is an integer from about 0 to about 5. $Z^8$ represents groups which block the ends of the silicone chains. Preferably, $R^{93}$ groups include methyl, ethyl, propyl, phenyl, methylphenyl and phenylmethyl, $Z^8$ groups include hydroxy, methyl, methoxy, ethoxy, propoxy, and aryloxy. More preferably, $R^{93}$ groups and $Z^8$ groups are methyl groups. The preferred volatile silicone compounds are hexamethyldisiloxane, octamethyltrisiloxane, decamethyltetrasiloxane, hexadecamethylheptasiloxane. Commercially available volatile silicone compounds useful herein include octamethyltrisiloxane with tradename SH200C-1cs, decamethyltetrasiloxane with tradename SH200C-1.5cs, hexadecamethylheptasiloxane with tradename SH200C-2cs, all available from Dow Corning.

The volatile silicone oils useful herein also include a cyclic silicone compound having the formula:

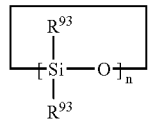

wherein $R^{93}$ is independently alkyl or aryl, and n is an integer of from 3 to 7.

Preferably, $R^{93}$ groups include methyl, ethyl, propyl, phenyl, methylphenyl and phenylmethyl. More preferably, $R^{93}$ groups are methyl groups. The preferred volatile silicone compounds are octamethylcyclotetrasiloxane, decamethylcyclopentasiloxane, tetradecamethylcyclohexasiloxane. Commercially available volatile silicone compounds useful herein include octamethylcyclotetrasiloxane with tradename SH244, decamethylcyclopentasiloxane with tradename DC245 and SH245, and dodeamethylcyclohexasiloxane with tradename DC246; all available from Dow Corning.

Non-volatile oils useful herein are, for example, tridecyl isononanoate, isostearyl isostearate, isocetyl isosteatrate, isopropyl isostearate, isodecyl isonoanoate, cetyl octanoate, isononyl isononanoate, diisopropyl myristate, isocetyl myristate, isotridecyl myristate, isopropyl myristate, isostearyl palmitate, isocetyl palmitate, isodecyl palmitate, isopropyl palmitate, octyl palmitate, caprylic/capric acid triglyceride, glyceryl tri-2-ethylhexanoate, neopentyl glycol di(2-ethyl hexanoate), diisopropyl dimerate, tocopherol, tocopherol acetate, avocado oil, camellia oil, turtle oil, macadamia nut oil, corn oil, mink oil, olive oil, rapeseed oil, eggyolk oil, sesame oil, persic oil, wheat germ oil, pasanqua oil, castor oil, linseed oil, safflower oil, cotton seed oil, perillic oil, soybean oil, peanut oil, tea seed oil, kaya oil, rice bran oil, china paulownia oil, Japanese paulownia oil, jojoba oil, rice germ oil, glycerol trioctanate, glycerol triisopalmiatate, trimethylolpropane triisostearate, isopropyl myristate, glycerol tri-2-ethylhexanoate, pentaerythritol tetra-2-ethylhexanoate, lanolin, liquid lanolin, liquid paraffin, squalane, vaseline, and mixtures thereof. Commercially available oils include, for example, tridecyl isononanoate with tradename Crodamol TN available from Croda, Hexalan available from Nisshin Seiyu, and tocopherol acetates available from Eisai.

Non-volatile oils useful herein also include polyalkyl or polyaryl siloxanes with the following structure (I)

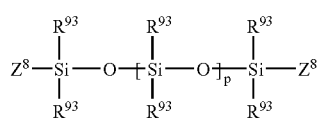

wherein $R^{93}$ is alkyl or aryl, and p is an integer from about 7 to about 8,000. $Z^8$ represents groups which block the ends of the silicone chains. The alkyl or aryl groups substituted on the siloxane chain ($R^{93}$) or at the ends of the siloxane chains $Z^8$ can have any structure as long as the resulting silicone remains fluid at room temperature, is dispersible, is neither irritating, toxic nor otherwise harmful when applied to the skin, is compatible with the other components of the composition, and is chemically stable under normal use and storage conditions. Suitable $Z^8$ groups include hydroxy, methyl, methoxy, ethoxy, propoxy, and aryloxy. The two $R^{93}$ groups on the silicon atom may represent the same group or different groups. Preferably, the two $R^{93}$ groups represent the same group. Suitable $R^{93}$ groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. These silicone compounds are available, for example, from the General Electric Company in their Viscasil® and SF 96 series, and from Dow Corning in their Dow Corning 200 series.

Polyalkylaryl siloxane fluids can also be used and include, for example, polymethylphenylsiloxanes. These siloxanes are available, for example, from the General Electric Company as SF 1075 methyl phenyl fluid or from Dow Corning as 556 Cosmetic Grade Fluid.

Non-volatile oils also useful herein are the various grades of mineral oils. Mineral oils are liquid mixtures of hydrocarbons that are obtained from petroleum. Specific examples of suitable hydrocarbons include paraffin oil, mineral oil, dodecane, isododecane, hexadecane, isohexadecane, eicosene, isoeicosene, tridecane, tetradecane, polybutene, polyisobutene, and mixtures thereof.

Non-volatile oils useful herein include cholesteryl derivatives made of cholesterol and a C12-22 fatty acid or hydroxy fatty acid having high water holding ability, preferably cholesteryl 12-hydroxystearate, cholesteryl macadamiate, Cholesteryl Stearate, and mixtures thereof. Commercially available cholesteryl derivatives include cholesteryl 12-hydroxystearate with tradename Salacos HS available from Nisshin Oil Mills, Ltd., and cholesteryl macadamiate with tradename YOFCO MAC available from Nippon Fine Chemical Co., Ltd.

Film Forming Agents

For providing color cosmetics having wear resistance, the carrier may contain a film forming agent.

The composition of the present invention may further contain a nonvolatile dispersed silicone usually referred to as silicone gum. The term "silicone gum", as used herein, means a polyorganosiloxane material having a viscosity at 25° C. of greater than or equal to 1,000,000 mPa·s. Silicone gums are believed to provide wearability improvement such as long-lasting effect. The "silicone gums" will typically have a mass molecular weight in excess of about 200,000, generally between about 200,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. Commercially available silicone gums are described in General Electric Silicone Rubber Product Data Sheets as SE 30, SE 33, SE 54 and SE 76.

The composition of the present invention may further contain a silicone resin, which are highly crosslinked polymeric siloxane systems. Silicone resins are believed to enhance spreadability and improve the feel to the skin. The crosslinking is introduced through the incorporation of tri-functional and tetra-functional silanes with mono-functional or di-functional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units, and hence, a sufficient level of crosslinking, such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinylchlorosilanes, and tetrachlorosilane, with the methyl substituted silanes being most commonly utilized. Preferred are crosslinked silicone powders with tradenames Trefil E-505C, Trefil E-506C, and 9506 Powder; suspensions of silicone elastomer powders with tradenames BY29-119 and BY29-122; and silicone compound emulsions with tradenames SH5500, SC5570, and SM 5571; all available from Dow Corning.

Other useful silicone resins are silicone resin powders such as the material given the CTFA designation polymethylsilsequioxane, which is commercially available as Tospearl™ from Toshiba Silicones.

Silicone materials and silicone resins in particular, can conveniently be identified according to a shorthand nomenclature system well known to those skilled in the art as the "MDTQ" nomenclature. Under this system, the silicone is described according to the presence of various siloxane monomer units which make up the silicone. Briefly, the symbol M denotes the mono-functional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetra-functional unit $SiO2$. Primes of the unit symbols, e.g., M', D', T', and Q' denote substituents other than methyl, and must be specifically defined for each occurrence. Typical alternate substituents include groups such as vinyl, phenyl, amino, hydroxyl, etc. The molar ratios of the various units, either in terms of subscripts to the symbols indicating the total number of each type of unit in the silicone, or an average thereof, or as specifically indicated ratios in combination with molecular weight, complete the description of the silicone material under the MDTQ system. Higher relative molar amounts of T, Q, T' and/or Q' to D, D', M and/or or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MQ and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000. Commercially available MQ resins are, for example, trimethyl siloxy silicate with tradename BY 11-018 available from Dow Corning.

Antiperspirant Active

For providing antiperspirant compositions, the carrier may contain an antiperspirant active such as aluminum/zirconium astringent complexes including aluminum halides, aluminum hydroxy-halides, zirconyl oxyhalides, zirconyl hydroxy-halides; and ZAG complexes such as aluminium zirconium trichlorohydrex gly.

Additional Emulsifiers

The carrier may contain an additional emulsifier for incorporating various materials as mentioned above. The additional emulsifier is selected by the artisan in view of the materials to be incorporated, and the stability of the obtained personal care composition. For providing liphophilic and/or anhydrous compositions, the additional emulsifiers are preferably also of lower HLB, typically less than about 8.

The additional emulsifier can be an ester-type surfactant. Ester-type surfactants useful herein include: sorbitan monoisostearate, sorbitan diisostearate, sorbitan sesquiisostearate, sorbitan monooleate, sorbitan dioleate, sorbitan sesquioleate, glyceryl monoisostearate, glyceryl diiostearate, glyceryl sesquiisostearate, glyceryl monooleate, glyceryl dioleate, glyceryl sesquioleate, diglyceryl diisostearate, diglyceryl dioleate, diglycerin monoisostearyl ether, diglycerin diisostearyl ether, and mixtures thereof.

Commercially available ester-type surfactants are, for example, sorbitan isostearate having a tradename Crill 6 available from Croda, and sorbitan sesquioleate with tradename Arlacel 83 available from Kao Atras.

The additional emulsifier can be a silicone-type surfactant. Silicone-type surfactants useful herein are (i), (ii), as shown below, and mixtures thereof.

(i) dimethicone copolyols having the structure:

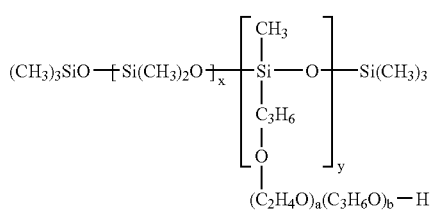

wherein x is an integer from 5 to 100, y is an integer from 1 to 50, a is zero or greater, b is zero or greater, the average sum of a+b being 1-100.

(ii) dimethicone copolyols having the structure:

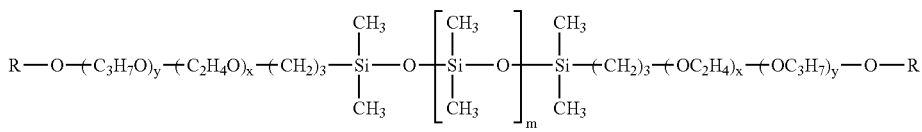

wherein R is selected from the group consisting of hydrogen, methyl, and combinations thereof, m is an integer from 5 to 100, x is independently zero or greater, y is independently zero or greater, the sum of x+y being 1-100.

Commercially available silicone-type surfactants are, for example, DC5225C, BY22-012, BY22-008, SH3746M, SH3771M, SH3772M, SH3773M, SH3775M, SH3748, SH3749, and DC5200, all available from Dow Corning.

Others

The carrier may include other additional components selected by the artisan according to the desired characteristics of the final product and which are suitable for rendering the composition more cosmetically or aesthetically acceptable or to provide them with additional usage benefits. Such additional components generally are used individually at levels of no more than about 5% by weight of the composition.

Other components which can be formulated into the compositions of the present invention are; preservatives such as benzyl alcohol, methyl paraben, propyl paraben, imidazolidinyl urea, and EDTA and its salts, perfumes, ultraviolet and infrared screening and absorbing agents such as ethylhexyl methoxycinnamate, whitening agents such as magnesium L-ascorbyl-2-phosphate and ascorbyl glucoside, MAXI-LIP which is an ethylhexyl palmitate-tribehenin-sorbitan isostearate-palmitoyl oligopeptide available from Sederma, mulberry root extract, yeast fermented filtrates, farnesol, and others.

EXAMPLES

The following examples further describe and demonstrate the preferred embodiments within the scope of the present invention. The examples are given solely for the purpose of illustration, and are not to be construed as limitations of the present invention since many variations thereof are possible without departing from its spirit and scope.

Examples 1-5

The following make-up compositions are formed by the following components using the method of preparation described herein:

| NO. | Component | Ex. 1 | Ex. 2 | Ex. 3 | Ex. 4 | Ex. 5 |
|---|---|---|---|---|---|---|
| 1 | Cetyl Dimethicone Copolyol *1 | 0.3 | 1.5 | 3 | 4 | 5 |
| 2 | Glycerin *2 | 0.7 | 3.5 | 7 | 6 | 10 |
| 3 | Niacinamide *3 | 0.2 | 1 | 2 | | |
| 4 | Urea *4 | | | | 5 | 7 |
| 5 | Cholesteryl Macadamiate *5 | 2 | 2 | 5 | | |
| 6 | Phenyl Trimethicone *6 | 15 | 10 | 10 | 2 | 5.3 |
| 7 | Liquid Petrolatum *7 | | | 2 | | 10 |
| 8 | Hydrogenated Polyisobutene *8 | 10 | | | | |
| 9 | Dimer Diol Esters *9 | 10 | | | | |
| 10 | Ozokerite *10 | 2 | 4 | 4 | 4 | 4 |
| 11 | Microcrystalline Wax *11 | 1 | 1.5 | 1.5 | 1.5 | 1.5 |
| 12 | Candelilla Wax *12 | | 5 | 5 | 5 | 3 |
| 13 | Polyethylene Wax *13 | 7 | | | | |
| 14 | Paraffin *14 | 3 | 3 | 3 | 3 | 2 |
| 15 | Diglyceryl Sebacate/Isopalmitate *15 | 14.05 | 18.5 | 11.5 | 11.5 | |
| 16 | Absorption Refined Lanolin *16 | 3 | 2.5 | 2.5 | 2.5 | 2.5 |
| 17 | Lanolin Oil *17 | | 20 | 20 | | |
| 18 | Trioctanoin *18 | 7 | 7 | 7 | 20 | 19.2 |
| 19 | Isotridecyl Isononanoate *19 | 3 | 3 | 3 | 5 | 10 |
| 20 | Octyl methoxycinnamate | 7.25 | | | | |
| 21 | MAXI-LIP ™ *20 | 1 | | | | |
| 22 | Farnesol *21 | 3 | | | | |
| 23 | Preservatives | 0.5 | 0.5 | 0.5 | 0.5 | 0.5 |
| 24 | Titanium Dioxide | 1 | 2 | 2 | 10 | 10 |
| 25 | Mica | 3 | 3 | 3 | 10 | 10 |
| 26 | Pearl Pigments | 1 | 5 | | | |
| 27 | Iron Oxides | 3 | 3 | 3 | 5 | 5 |
| 28 | Laked Color Dyes | 2 | 2 | 2 | | |

Definitions of Components
*1 Cetyl Dimethicone Copolyol; ABIL EM90 available from Goldschmidt
*2 Glycerin: Glycerin USP available from Asahi Denka
*3 Niacinamide: Niacinamide available from Roche
*4 Urea: Urea available from Taisei Chemical
*5 Cholesteryl Macadamiate: YOFCO MAC available from Nippon Fine Chemical
*6 Phenyl Trimethicone: Silicone Oil DC556 available from TORAY DOW CORNING SILICONE
*7 Liquid Petrolatum: Liquid Petrolatum available from Witco Chemical
*8 Hydrogenated Polyisobutene: Parlream 18 available from NOF Chemical
*9 Dimer Diol Esters: Lusplun available from Nippon Fine Chemical
*10 Ozokerite: Ozokerite wax SP-1021 available from Strahl & Pitsh
*11 Microcrystalline Wax: Multiwax 180-M Yellow available from Witco Chemical
*12 Candelilla wax: Candelilla wax NC-1630 available from CERA RICA NODA Co., LTD
*13 Polyethylene Wax: Performalene PL available from Nikko Chemical
*14 Paraffin: Paraffin wax FT-150 available from Sazole
*15 Diglyceryl Sebacate/Isopalmitate: Salacos DGS-16 available from Nisshin Oil Mills
*16 Absorption Refined Lanolin: Crodalan SWL available from Croda
*17 Lanolin Oil: Lanolin Oil available from Croda
*18 Trioctanoin: Hexalan available from Nisshin Oil Mills, Ltd.
*19 Isotridecyl Isononanoate: Crodamol TN available from Croda
*20 MAXI-LIP ™: ethylhexyl palmitate-tribehenin-sorbitan isostearate-palmitoyl oligopeptide available from Sederma
*21 Farnesol: farnesol available from DRAGOCO Method of Preparation The make-up compositions of Examples 1-5 are suitably prepared as follows: First, a mixture of component numbers 2 through 4 are heated to dissolve at a low speed using a Disper at about 80° C. After dissolving, component number 1 is added to the mixture of component numbers 2-4, and further dispersed at a speed of from 1000 rpm to 3000 rpm using a Disper to form a polyol-in-silicone emulsion. Separately, component numbers 5 through 28 are heated to dissolve at about 85° C. in a tank, followed by adding the above obtained polyol-in-silicone emulsion, and the mixture is dispersed at about 85° C. using a Disper. The composition thus is adjusted to a temperature of about 85° C. Finally, the dispersion is filled in an air-tight container and allowed to cool to room temperature.

These embodiments represented by the previous examples have many advantages. For example, Examples 1 through 3 provide lipsticks which provide; improved stability with regard to physical hardness, color, and sweat resistance, improved lip suppleness, moisturization, and reduction of visible liplines and wrinkles to the lips. Example 4 provides a stick foundation. Example 5 provides a poured foundation. The foundations of Examples 4 and 5 provide; improved stability with regard to color, and sweat resistance, improved suppleness, moisturization, and reduction of visible lines and wrinkles to the skin, particularly facial skin.

It is understood that the examples and embodiments described herein are for illustrative purposes only and that various modifications or changes in light thereof will be suggested to one skilled in the art without departing from its spirit and scope.

All documents cited in the Detailed Description of the Invention are, in relevant part, incorporated hereby by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A lipstick composition comprising:
    (a) from about 0.01% to about 65% of a polyol-in-silicone emulsion consisting essentially of:
        (i) an alkyl dimethicone copolyol having an HLB of from about 4 to about 6, and a molecular weight of from about 10,000 to about 20,000, wherein the alkyl group is made of about 10 to about 22 carbons; and
        (ii) a polyol, wherein the weight ratio of the alkyl dimethicone copolyol to the polyol is from about 100:1 to about 2:8,
    (b) a carrier comprising a solid wax, an oil and a pigment.

2. The lipstick composition of claim 1 comprising by weight:
    from about 0.1% to about 20% of the polyol-in-silicone emulsion;
    from about 10% to about 20% of the solid wax;
    from about 30% to about 80% of the oil; and
    from about 2% to about 20% of the pigment.

3. A foundation composition comprising:
    (a) from about 0.01% to about 65% of a polyol-in-silicone emulsion consisting essentially of:
        (i) an alkyl dimethicone copolyol having an HLB of from about 4 to about 6, and a molecular weight of from about 10,000 to about 20,000, wherein the alkyl group is made of bout 10 to about 22 carbons; and
        (ii) a polyol, wherein the weight ratio of the alkyl dimethicone copolyol to the polyol is from about 100:1 to about 2:8,
    (b) a carrier comprising an oil and a pigment.

4. The foundation composition of claim 3 wherein the carrier further comprises a film forming agent.

5. A make-up remover composition comprising:
    (a) from about 0.01% to about 65% of a polyol-in-silicone emulsion consisting essentially of:
        (i) an alkyl dimethicone copolyol having an HLB of from about 4 to about 6, and a molecular weight of from about 10,000 to about 20,000, wherein the alkyl group is made of about 10 to about 22 carbons; and
        (ii) a polyol, wherein the weight ratio of the alkyl dimethicone copolyol to the polyol is from about 100:1 to about 2:8,
    (b) a carrier comprising a detersive surfactant and water.

* * * * *